(12) United States Patent
Sutariya et al.

(10) Patent No.: US 10,973,776 B1
(45) Date of Patent: Apr. 13, 2021

(54) LOTEPREDNOL ETABONATE NANOPARTICLES IN THERMOREVERSIBLE GELS FOR ENHANCED THERAPEUTICS

(71) Applicant: University of South Florida, Tampa, FL (US)

(72) Inventors: Vijaykumar Bhadabhai Sutariya, Tampa, FL (US); Anjali A. Hirani, Orlando, FL (US); Yashwant V. Pathak, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/892,423

(22) Filed: Jun. 4, 2020

Related U.S. Application Data

(63) Continuation of application No. 15/243,376, filed on Aug. 22, 2016, now Pat. No. 10,729,663.

(60) Provisional application No. 62/207,997, filed on Aug. 21, 2015, provisional application No. 62/208,187, filed on Aug. 21, 2015.

(51) Int. Cl.
*A61K 9/70* (2006.01)
*A61K 31/58* (2006.01)
*A61K 31/56* (2006.01)

(52) U.S. Cl.
CPC ............ *A61K 9/7015* (2013.01); *A61K 31/56* (2013.01); *A61K 31/58* (2013.01)

(58) Field of Classification Search
CPC ....... A61K 31/56; A61K 31/58; A61K 9/7015
See application file for complete search history.

(56) References Cited

U.S. PATENT DOCUMENTS

| | | | | |
|---|---|---|---|---|
| 2004/0151754 | A1* | 8/2004 | Ashton | A61K 9/0051 424/427 |
| 2013/0316001 | A1* | 11/2013 | Popov | A61K 9/0048 424/490 |

OTHER PUBLICATIONS

Sutariya et al. Thermoreversible gel for delivery of activin receptor-like kinase 5 inhibitor SB-505124 for glaucoma filtration surgery. Pharm Dev Technol. 2013. vol. 18 (No. 4): 957-962.
Tamboli et al., Novel pentablock copolymer (PLA-PCL-PEG-PCL-PLA) based nanoparticles for controlled drug delivery: effect of copolymer compositions on the crystallinity of copolymers and in vitro drug release profile from nanoparticles. Colloid Polym Sci. 2013. vol. 291: 1235-1245.
Thrimawithana et al., Drug delivery to the posterior segment of the eye: challenges and opportunities. Drug Deliv Lett. 2011. vol. 1: 40-44.
Thrimawithana et al., Drug delivery to the posterior segment of the eye. Drug Discov Today. 2011. vol. 16 (Nos. 5-6): 270-277.
Urtti. Challenges and obstacles of ocular pharmacokinetics and drug delivery. Adv Drug Deliv Rev. 2006. vol. 58:1131-1135.
Vodithala et al., Development and evaluation of thermoreversible ocular gels of ketorolac tromethamine. Int J Biopharm. 2010. vol. 1 (No. 1):39-45.
Wang et al., Inhibitory effects of triamcinolone acetonide on bFGF-induced migration and tube formation in choroidal microvascular endothelial cells. Graefe's archive for clinical and experimental Ophthalmology. 2002. vol. 240: 42-48.
Wu et al., Dexamethasone induction of keloid regression through effective suppression of VEGF expression and keloid fibroblast proliferation. J Investig Dermatol 2006;126: 1264-1271.
Yasukawa et al., Drug delivery systems for vitreoretinal diseases. Progr Retinal Eye Res. 2004. vol. 23: 253-281.
Yoncheva and Lambov., Development of biodegradable poly(alpha-methylmalate) microspheres. Pharmazie. 2000. vol. 55 (No. 2): 148-50.
Zhang et al., Model of transient drug diffusion across cornea. J Control Release. 2004. vol. 99: 241-258.
Boddu et al., Novel Nanoparticulate Gel Formulations of Steroids for the Treatment of Macular Edema. Journal of Ocular Pharmacology and Therapeutics, 2010. vol. 26, No. 1: 37-48.
Costa et al., Case-control study of subconjunctival triamcinolone acetonide injection vs intravenous methylprednisolone pulse in the treatment of endothelial corneal allograft rejection. Eye (2009) 23, 708-714.
Pamujula et al., Cellular delivery of PEGylated PLGA nanoparticles. J. Pharm Pjarmacol. Jan. 2012; 64(1): 61-67.
Sutter et al., Intravitreal Triamcinolone for Radiation-Induces Macular Edema. Ophthalmol. Oct. 2013, vol. 121: 1491-1493.
Bala et al., PLGA nanoparticles in drug delivery: the state of the art. Crit Rev Ther Drug Carrier Syst. 2004. vol. 21 (No. 5): 387-422.
Bejjani et al. Nanoparticles for gene delivery to retinal pigment epithelial cells. Mol Vis. 2005. vol. 11: 124-32.
Bodor et al., A comparison of intraocular pressure elevating activity of loteprednol etabonate and dexamethasone in rabbits. Curr Eye Res. 1992. vol. 11 (No. 6): 525-30.
Bodor et al., Metabolism, distribution, and transdermal permeation of a soft corticosteroid, loteprednol etabonate. Pharm Res. 1992. vol. 9 (No. 10): 1275-1278.
Bourges et al. Ocular drug delivery targeting the retina and retinal pigment epithelium using polylactide nanoparticles. Invest Ophthalmol Visual Sci. 2003. vol. 44 (No. 8): 3562-3569.
Bu et al. Ocular disposition, pharmacokinetics, efficacy and safety of nanoparticle-formulated ophthalmic drugs. Curr Drug Metab. 2007. vol. 8: 91-107.

(Continued)

*Primary Examiner* — Jennifer A Berrios
(74) *Attorney, Agent, or Firm* — Molly L. Sauter; Smith & Hopen, P.A.

(57) ABSTRACT

The present invention provides a sustained drug delivery system for the treatment of age-related macular degeneration (AMD), comprising corticosteroid encapsulated nanoparticles incorporated into a thermoreversible hydrogel. The corticosteroid may be triamcinolone acetate (TA), dexamethasone, or loteprednol etabonate (LE). The proposed drug delivery system is nontoxic to ARPE-19 (retinal pigment epithelium) cells and significantly reduces VEGF (vascular endothelial growth factor) expression as compared to solutions of the coticosteroids. The present invention provides sustained delivery of the corticosteroid to the posterior segment of the eye, reducing the frequency of intraocular injections necessary to maintain therapeutic concentrations.

8 Claims, 9 Drawing Sheets

(56) References Cited

OTHER PUBLICATIONS

Budhian et al., Haloperidol-loaded PLGA nanoparticles: Systematic study of particle size and drug content. Int J Pharm. 2007. vol. 336: 367-375.

Buschini et al. Age related macular degeneration and drusen: neuroinflammation in the retina. Prog Neurobiol. 2011. vol. 95: 14-25.

Bylsma and Guymer. Treatment of age-related macular degeneration. Clin Exp Optomet 2005. vol. 88 (No. 5): 322-334.

Carroll et al. Brain-targeted delivery of Tempol-loaded nanoparticles for neurological disorders. J Drug Target 2010. vol. 18 (No. 9): 665-674.

Choi et al. In situ thermal gelling polypeptide for chondrocytes 3D culture. Biomaterials. 2010. vol. 31: 9266-9272.

Ciulla et al., Intravitreal triamcinolone acetonide inhibits choroidal neovascularization in a laser-treated rat model. Arch Ophthalmol. 2001. vol. 119: 399-404.

Coffey et al. Development of a non-settling gel formulation of 0.5% loteprednol etabonate for anti-inflammatory use as an ophthalmic drop. Clin Ophthalmol. 2013. vol. 7: 299-312.

Comstock and DeCory. Advances in corticosteroid therapy for ocular inflammation: Loteprednol etabonate. Int J inflammation. 2012. Article ID 789623: 1-12.

Comstock et al., Safety and efficacy of loteprednol etabonate ophthalmic ointment 0.5% for the treatment of inflammation and pain following cataract surgery. Clin Ophthalmol. 2011. vol. 5: 177-86.

Duvvuri et al. Development of a novel formulation containing poly (d, l-lactide-co-glycolide) microspheres dispersed in PLGA-PEG-PLGA gel for sustained delivery of ganciclovir. J Controlled Release. 2005. vol. 108: 282-293.

Fernandez-Robredo et al. Current treatment limitations in age-related macular degeneration and future approaches based on cell therapy and tissue engineering. J Ophthalmol. 2014. Article ID:510285: 1-13.

Ferrara et al., The biology of VEGF and its receptors. Nat Med. 2003. vol. 9 (No. 6): 669-676.

Gambhire et al., In Situ Hydrogel: Different Approaches to ocular drug delivery. Int J Pharm Pharm Sci. 2013. vol. 5 (Issue 2): 27-36.

Gary et al., Controlled evaluation of loteprednol etabonate and prednisolone acetate in the treatment of acute anterior uveitis. Am J Ophthalmol. 1999. vol. 127: 537-44.

Gaudana et al., Ocular drug delivery. AAPS J. 2010. vol. 12 (No. 3): 348-60.

Geldenhuys et al., Brain-targeted delivery of paclitaxel using glutathione-coated nanoparticles for brain cancers. J Drug Targeting. 2011. vol. 19 (No. 9): 837-845.

Gomez-Gaete et al., Encapsulation of dexamethasone into biodegradable polymeric nanoparticles. Int J Pharm. 2007. vol. 331: 153-159.

Gopal and Sharma. Use of intravitreal injection of triamcinolone acetonide in the treatment of age-related macular degeneration. Ind J Ophthalmol. 2007. vol. 55 (No. 6): 431-435.

Group MPS. Laser photocoagulation of subfoveal neovascular lesions of age-related macular degeneration: updated findings from two clinical trials. Arch Ophthalmol. 1993. vol. 111: 1200-1209.

Hirani et al., Triamcinolone acetonide nanoparticles incorporated in thermoreversible gels for age-related macular degeneration. Pharm Dev Technol. 2016. vol. 21 (No. 1): 61-67.

Ilyas et al., Longterm safety of loteprednol etabonate 0.2% in the treatment of seasonal and perennial allergic conjunctivitis. Eye & Contact Lens. 2004. vol. 30 (No. 1): 10-13.

Kadam et al., Influence of choroidal neovascularization and biodegradable polymeric particle size on transscleral sustained delivery of triamcinolone acetonide. Int J Pharm. 2012. vol. 434 (Nos. 1-2):140-147.

Kassem et al., Nanosuspensions as an ophthalmic delivery system for certain glucocorticoid drugs. Int J Pharm. 2007. vol. 340: 126-33.

Kreppel and Kochanek. Modification of adenovirus gene transfer vectors with synthetic polymers: a scientific review and technical guide. Mol Ther. 2008. vol. 16 (No. 1): 16-29.

Li et al., Controlled release of bevacizumab through nanospheres for extended treatment of age-related macular degeneration. Open Ophthalmol J. 2012. vol. 6: 54-58.

Majithiya et al., Thermoreversible-mucoadhesive gel for nasal delivery of sumatriptan. AAPS PharmSciTech. 2006. vol. 7 (No. 3): E1-E7.

McGhee et al., Locally administered ocular corticosteroids. Drug Safety. 2002. vol. 25 (No. 1): 33-55.

Moghimipour et al., Formulation and in vitro evaluation of topical liposomal gel of triamcinolone acetonide. Res J Pharma Biol Chem Sci. 2013. vol. 4 (Issue 1): 101-107.

Nirmal et al., In-situ gel: new trends in controlled and sustained drug delivery system. Int J PharmTech Res. 2010. vol. 2 (No. 2): 1398-1408.

Normand et al., VP22 light controlled delivery of oligonucleotides to ocular cells in vitro and in vivo. Mol Vis. 2005. vol. 11: 184-191.

Nowak. Age-related macular degeneration (AMD): pathogenesis and therapy. Pharmacol Rep. 2006. vol. 58: 353-363.

Park et al., An anti-angiogenic reverse thermal gel as a drug-delivery system for age-related wet macular degeneration. Macromol Biosci. 2013. vol. 13: 464-469.

Park et al., New approach of anti-VEGF agents for age-related macular degeneration. J Ophthalmol. 2012. Article ID:637316: 1-7.

Patel et al., Ocular drug delivery systems: an overview. World J Pharmacol. 2013. vol. 2 (No. 2): 47-64.

Patel et al., Tailor-made pentablock copolymer based formulation for sustained ocular delivery of protein therapeutics. J Drug Deliv. 2014. Article ID: 401747: 1-15.

Peyman et al., Intravitreal injection of therapeutic agents. Retina. 2009. vol. 29: 875-912.

Zhou et al., Nanoparticles in the ocular drug delivery. Int J Ophthalmol. 2013. vol. 6 (No. 3): 390-396.

Regatieri et al., Experimental treatments for neovascular age-related macular degeneration. In: Ying G-S, ed. Age related macular degeneration—the recent advances in basic research and clinical care. Rijeka, Croatia. InTech. 2012. Chapter 5: 83-98.

Sabzevari et al., Polymeric triamcinolone acetonide nanoparticles as a new alternative in the treatment of uveitis: In vitro and in vivo studies. Eur J Pharm Biopharm. 2013. vol. 84: 63-71.

Saraiya and Goldstein. Dexamethasone for ocular inflammation. Expert Opin Pharmacother. 2011. vol. 12 (No. 7): 1127-1131.

Sherif and Pleyer. Corticosteroids in ophthalmology: past-present-future. Ophthalmologica. 2002. vol. 216: 305-315.

Da Silva et al., Implants as drug delivery devices for the treatment of eye diseases. Brazilian J Pharm Sci. 2010. vol. 46 (No. 3): 585-595.

Spaide et al., Combined photodynamic therapy with verteporfin and intravitreal triamcinolone acetonide for choroidal neovascularization. Ophthalmology. 2003. vol. 110: 1517-1525.

Suen and Chau. Specific uptake of folate-decorated triamcinolone-encapsulating nanoparticles by retinal pigment epithelium cells enhances and prolongs antiangiogenic activity. J Control Release. 2013. vol. 167: 21-28.

* cited by examiner

LOTEPREDNOL ETABONATE NANOPARTICLES IN THERMOREVERSIBLE GELS FOR ENHANCED THERAPEUTICS

CROSS REFERENCE TO RELATED APPLICATION

This application claims priority to pending U.S. patent application Ser. No. 15/243,376, entitled "Nanoparticles in Thermoreversible Gels for Enhanced Therapeutics" filed on Aug. 22, 2016, which claims priority to U.S. Provisional Patent Application No. 62/207,997, entitled "Triamcinolone Acetonide Nanoparticles In Thermoreversible Gels For Enhanced Therapeutics", filed on Aug. 21, 2015, and U.S. Provisional Patent Application No. 62/208,187, entitled "Loteprednol Etabonate Nanoparticles In Thermoreversible Gels For Enhanced Therapeutics", filed on Aug. 21, 2015, the contents of which are herein incorporated by reference.

BACKGROUND OF THE INVENTION

Age-related macular degeneration (AMD) is the leading cause of visual loss in adults over the age of 50. Neovascular AMD is characterized by choroidal neovascularization (CNV), the growth of abnormal blood vessels under the retina which can leak blood and fluid, causing deterioration to the macula over time. Current treatment involves frequent intravitreal injections resulting in side effects, such as retinal detachment and low patient compliance.

Accordingly, a method of sustained drug delivery for the treatment of AMD is needed in the art that does not result in undesirable side effects or low patient compliance.

SUMMARY OF INVENTION

The present invention provides a sustained drug delivery system and method for the treatment of age-related macular degeneration. In various embodiments, the drug delivery system of the present invention includes corticosteroid encapsulated nanoparticles incorporated into a thermoreversible gel. The corticosteroid used may include triamcinolone acetate (TA), loteprednol etabonate (LE) and dexamethasone. This is not intended to be limiting and other corticosteroids are within the scope of the present invention.

In one embodiment of the present invention, triamcinolone acetonide (TA) is encapsulated by poly(ethylene glycol)-ylated (PEGylated) poly-(lactide-co-glycolide) (PLGA) nanoparticles (NPs) and incorporated into a PLGA-PEG-PLGA thermoreversible gel for the treatment of AMD. The TA-loaded NPs are prepared using the nanoprecipitation method and characterized for basic parameters. The TA-loaded NPs show an average particle size of 208.00±1.00 nm and polydispersity index of 0.005±0.001. In a particular embodiment, the 20% (w/v) thermoreversible gel is prepared using the cold method. MTT cytotoxicity data show that the drug delivery system was not cytotoxic on ARPE-19 cells as opposed to an equivalent concentration of TA alone. In vitro release analysis demonstrates that free TA was completely released within 48 hours; whereas 94% of TA was released from drug delivery system after 7 days. The proposed delivery system for TA is effective for sustained release treatment of ocular dysfunction.

In another embodiment, the present invention provides a sustained drug delivery system for the treatment of AMD which is comprised of loteprednol etabonate, poly(ethylene glycol)-ylated (PEGylated) poly-(lactide-co-glycolide) (PLGA) nanoparticles (NPs), and a PLGA-PEG-PLGA thermoreversible gel. This embodiment of the present invention provides sustained delivery of loteprednol etabonate to the posterior segment of the eye, thereby reducing the frequency of intraocular injections necessary to maintain therapeutic concentrations. In this particular embodiment of the present invention, the proposed drug delivery system is characterized for drug release, cytotoxicity studies and vascular endothelial growth factor (VEGF) suppression efficacy studies using ARPE-19 cells. The nanoparticles show uniform size distribution with mean size of 168.60±23.18 nm and exhibit sustained drug release. Additionally, the proposed drug delivery system is noncytotoxic to ARPE-19 cells and significantly reduced VEGF expression, as compared to loteprednol etabonate solution. These results suggest that the proposed drug delivery system comprised of loteprednol etabonate, poly(ethylene glycol)-ylated (PEGylated) poly-(lactide-co-glycolide) (PLGA) nanoparticles (NPs), and a PLGA-PEG-PLGA thermoreversible gel can be used for treating AMD, thereby reducing intravitreal administration frequency.

As such, the present invention provides sustained delivery of triamcinolone acetonide and loteprednol etabonate to the posterior segment of the eye, thereby reducing the frequency of intraocular injections necessary to maintain therapeutic concentrations.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
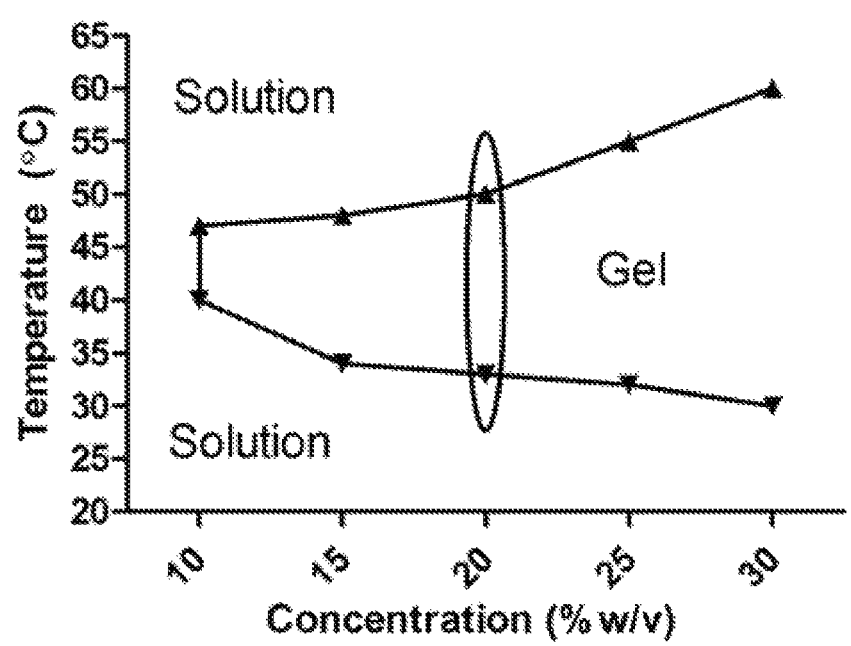
FIG. 1 is a graphical illustration of the temperature-dependent phase transitions in PLGA-PEG-PLGA thermoreversible gels based on w/v concentration of gel in aqueous solution, in accordance with an embodiment of the present invention.

AMD, a progressive, inflammatory eye disease, is one of the leading causes of blindness. It has been estimated that 36.8 million people suffered from some sort of vision loss due to eye diseases in the United States in 2010. AMD affects the posterior segment of the eye by damaging retinal pigment epithelium (RPE) cells which leads to a loss of central, focused vision through the abnormal growth of blood vessels damaging the macula of the retina, the area responsible for fine vision. The presence of intraocular debris may induce an inflammatory response which may cause further damage to the retina through the induction of a sustained immune response. Advanced AMD is characterized by choroidal neovascularization (CNV), the growth of abnormal blood vessels beneath the RPE or between the RPE and retina, accompanied by fluid and blood rupturing Bruch's membrane into the subretinal space and leading to retinal irregularities. Physical ocular barriers and routes of treatment pose limitations to therapeutic intervention in treating AMD.

Anti-angiogenic therapy is useful in slowing the progression of AMD due to the neovascularization characteristic of the disease. Vascular endothelial growth factor A (VEGF-A) is the most potent promoter of angiogenesis and vascular permeability, and its role in the pathogenesis of neovascular AMD is well recognized. VEGF-A levels are elevated in human CNV, and its vitreous levels have been reported to be increased when compared to healthy controls. VEGF is a potential pharmaceutical target; elevated VEGF levels can increase inflammation via inducing inflammatory mediators like intercellular adhesion molecule-1 (ICAM-1) and subsequently lead to the breakdown of the blood-retinal barrier (BRB).

The anatomy of the eye is a challenging part of the body for drug delivery. The posterior segment of the eye consists of the retina, vitreous and choroid. Topical treatment can easily access the anterior portion of the eye; however, multiple physical barriers and clearance mechanisms prevent easy access to the posterior segment of the eye. The topical route is the most favored and convenient for drug delivery, but nasolacrimal drainage and systemic absorption result in a poor drug bioavailability. A model of transient diffusion has shown that less than 5% of a lipophilic drug and 0.5% of a hydrophilic drug reach the anterior chamber. The bioavailability of the drug further decreases across the sclera, choroid and RPE. Drug permeability through the sclera is reduced with cationic and lipophilic solutes, and RPE have tight intercellular junctions to prevent the permeation of hydrophilic molecules. Furthermore, the lymphatic system, blood vessels and active transporters all work to clear drugs administered through transscleral routes. Drug delivery through systemic administration requires high doses to obtain a therapeutic concentration in the posterior segment of the eye due to the tight barriers in RPE. Intravitreal injections circumvent the physiological barriers and maintain therapeutic doses without damaging bystander tissue; however, frequent injections can lead to complications like retinal detachment, increase in ocular pressure and hemorrhage. Given the presence of these physiological barriers, the development of therapies that efficiently, deliver drugs and extend drug release to the posterior segment of the eye would be beneficial to the progression of ocular disease treatment.

Although current therapies exist to slow the progression of AMD, alternative drug delivery systems (DDS) are needed to enhance the therapeutic profiles of these drugs. Nanoparticles (NP) have been studied as drug carriers in ocular pharmaceuticals. They, can be made from biodegradable, polymeric materials in which drugs can be dissolved, entrapped or adsorbed. The major benefits of implementing NPs for ocular drug delivery are: (1) ease of administration via injection due to the size of the particle, (2) smaller particles are well tolerated in the eye, (3) particles of the nanometer range have shown increased solubility, surface area and drug dissolution, (4) NPs can be manipulated by polymer's weight and hydrophilicity to allow sustained drug release and (5) particles approximately 200 nm in size can be localized in RPE cells. In addition, recent studies have shown that after intravitreal injections, a majority of NPs were localized at the RPE within 6 h and cytoplasmic concentrations of the NP remained elevated for as long as 4 months.

Poly(lactide-co-glycolic acid) (PLGA) is an FDA-approved polymer that has been studied due to its biocompatibility and toxicity. The rate of degradation can be manipulated by the polymer's molecular weight, hydrophilicity and ratio of lactide to glycolide to extend the release time of associated drugs. PLGA NPs have been shown to have controlled drug release, low cytotoxicity and few side effects. Polyethylene glycol (PEG) has a slow clearance from the blood, allowing an increased drug release and reducing PLGA NP uptake by the reticulo-endothelial system (RES) when chemically conjugated to the PLGA vector as compared to non-conjugated PLGA. PEGylated PLGA NPs of bevacizumab, an anti-VEGF antibody, have shown sustained release of the drug over 60 days.

Thermoreversible hydrogels (TR gels) are a subtype of in situ gels that can be administered as a solution and undergo gelation with specific stimuli. Specifically, TR gels are biodegradable, water soluble polymers that undergo phase transitions upon temperature elevation. The gel can be loaded with bioactive macromolecules and pharmacological agents irrespective of their solubility properties. Localized and sustained release can be achieved due to the gel's quick formation in vivo. Their improved bioavailability and ease of administration make them an attractive DDS. Studies have shown the synthesis of an ABA-type block copolymer, polyethylene glycol)-poly(serinol hexamethylene urethane), to release bevacizumab. The in vitro drug release profile achieved a longer therapeutic window over 17 weeks. Such treatments could potentially reduce the frequency of intravitreal injections. An alternative formulation includes Pluronic F 127 as the thermoreversible polymer and methyl cellulose as a release controlling agent. This formulation has been used to deliver nonsteroidal anti-inflammatory drugs for conjunctivitis as well as selective inhibitors for glaucoma.

Triamcinolone acetate (TA), a synthetically modified glucocorticoid, is utilized for its anti-inflammatory and immunomodulatory effects against a number of diseases. TA is commonly used in conjunction with other drugs and acts by binding steroid receptors in cells and subsequently inducing or repressing target genes, thus leading to an inhibition of inflammatory processes, such as edema and vascular permeability.

TA, and similar glucocorticoids, also act on vascular endothelial growth factor (VEGF) by inhibiting its secretion and inhibiting cytokine production. Such drugs can also inhibit basic fibroblast growth factor (bFGF) along with decreasing the VEGF levels characteristic of neovascularization. TA is known to inhibit laser-induced choroidal neovascularization in rats as well as improve visual acuity when injected intravitreally.

However, high doses of TA and similar steroids may lead to adverse effects such as increased intraocular pressure and the formation of cataracts. TA is clinically used intravitreally against neovascularization in age-related macular degeneration (AMD).

In one embodiment, the present invention describes the preparation of TA-encapsulated PLGA-PEG NPs incorporated into TR gel to improve the therapeutic profile of TA in AMD. It is shown that the NP size is appropriate for intracellular uptake, the NPs and TR gel demonstrate a sustained release of the drug over 10 days, the NP and TR gel vectors are non-toxic in ARPE-19 cells, and the NP and TR gel DDS are able to reduce VEGF levels in ARPE-19 cells. These results suggest that the proposed DDS has the potential to significantly improve current therapies against AMD.

In an exemplary embodiment of the present invention, Poly(lactic-co-glycolic acid) (PLGA) conjugated with polyethylene glycol (PEG) (PEG-PLGA) (5050 DLG, mPEG 5000, 5 wt % PEG) was purchased from Lakeshore Biomaterials (Birmingham, Ala.). Triamcinolone acetonide was purchased from Alfa Aesar (Ward Hill, Mass.). Poly(lactide-co-glycollide)-b-Poly(ethyleneglycol)-b-Poly(lactide-co-glycolide) [PLGA-PEG-PLGA (Mn~100:1,000:1,100 Da, 3:1 LA:GA) (25% PEG)] thermogelling polymer was purchased from Polyscitech (West Lafayette, Ind.). Phosphate-buffered saline (PBS) solution was purchased from Mediatech, Inc (Manassas, Va.). Thiazolyl blue tetrazolium bromide (MTT reagent), acetone and methanol were purchased from Sigma Aldrich (St. Louis, Mo.). All other chemicals used in this exemplary embodiment were of analytical grade and were used without any further purification, unless specified.

In the exemplary embodiment, TA NPs were prepared using a previously reported nanoprecipitation method. Briefly, 22 mg of TA and 110 mg of PEGylated PLGA were dissolved in 2 ml acetone (organic phase), and the resulting solution was added dropwise to 20 ml of deionized H2O (40° C.) spinning at 300 rpm overnight to allow the full evaporation of the organic phase and the formation of the NP suspension. The NPs were separated by centrifugation at 3000 rpm for 10 min and resuspended in fresh deionized H2O.

The NP parameters were studied by measuring the particle size and polydispersity index (PDI). The effect of loading TA into the NPs on these parameters was studied by, comparing TA NPs to blank NPs. Particle size and PDI were measured using the Dynamic Pro plate reader (Wyatt Technology Corporation, Santa Barbara, Calif.). The NP samples were diluted 1:5 in deionized water to fit instrument specifications.

Drug encapsulation efficiency was determined using a previously reported method. 1 ml of the NP solution was centrifuged at 12 000 rpm for 5 min. The supernatant was removed and was replaced with 1 ml of methanol and stored at 4° C. overnight. The supernatant of the NP/methanol solution was diluted 1:5 times and measured by UV spectroscopy at a wavelength of 240 nm ($\lambda_{max}$). The supernatant was analyzed and compared to a series of standard dilutions of TA in methanol ($r^2$=0.99764). Encapsulation efficiency was determined using the following equation:

$$\% \text{ Entrapment efficiency} = \frac{\text{Actual drug amount}}{\text{Theoretical drug amount}} \times 100$$

TR gels were prepared using the cold method. To prepare 20% w/v gel, 100 mg of PLGA-PEG-PLGA gel was solubilized in deionized H2O overnight at 4° C. Different percentages of the gel (10, 15, 20, 25 and 30% w/v) were screened for the most optimal gelation temperature.

Gelation temperature was detected by visual inspection using a previously published method. Aqueous solutions of the gel (10, 15, 20, 25 and 30% wily) were prepared in distilled deionized $H_2O$, and 500 mL of each solution was heated from 10 to 60° C. At each 1° C. interval, the tubes were inverted to investigate flow properties. Solutions were considered to be in the gel state if no flow was observed following tube inversion.

The rate of TA release from the NPs was measured by adapting a previously reported method. Dialysis membrane tubing, MWCO 10 000 Da. (Spectrum Laboratories, Rancho Dominguez, Calif.) was soaked in deionized 1120 overnight. 1 ml of the NP suspension was added to the dialysis membrane tubing after being briefly sonicated and was placed into 100 ml of PBS covered and stirring at 100 rpm at 37° C. 1 mL samples were removed at predetermined intervals over 10 days and replaced with fresh PBS. Samples were analyzed using UV spectroscopy at a wavelength of 240 nm ($\lambda$max) and compared to standard dilutions of TA in PBS ($r^2$=0.989) to determine the percentage of drug released over 10 days.

The rate of TA release from the TR gel was measured by dispersing TA NPs in 200 ml of 20% w/v polymer solution and allowed to gel by placing in incubator at 37° C. for 5 min. After gelling, release was initiated by adding 2.5 ml PBS. 1 ml samples were removed at predetermined intervals over 10 days and replaced with fresh PBS.

Human retinal pigment epithelium, ARPE-19, cells (ATCC # CRL-2302) were grown in 1:1 Dulbecco's Modified Eagle's Medium and Ham's F12 Medium (Mediated, Inc., Manassas, Va.) with 10% fetal bovine serum and 100 Um' penicillin/streptomycin (Sigma Aldrich, St. Louis, Mo.). The cultures were maintained in a humid environment at 5% $CO_2$ and 37° C.

The cytotoxicity of the DDS was assessed in ARPE-19 cells by the 3-(4,5-dimethylthiazol-2-yl)-2,5-diphenyltetrazolium bromide salt (MTT) assay. Briefly, cells were seeded in 24-well plates at a density of 5×104 cells/ml for 24 h to achieve confluency before treatment. Cells were exposed to free TA, TA NPs, and TA NP-TR gel at varying concentrations (0, 1, 10, 100 μM) for 24 h after which the MTT assay was performed. Cell culture media were aspirated, and 500 ml of MTT reagent solution (1 mg/ml) was added to each well. Cells were incubated at 37° C. and 5% $CO_2$ for 4 h, after which the MTT reagent solution was aspirated and 1 mL of DMSO was added to each well. Plates were allowed to shake gently for 10 min before being read by Synergy H4 plate reader (Biotek Industries, Inc., Winooski, Vt.) at absorbance of 570 nm.

ARPE-19 cells were seeded onto 24-well plates at 5×104 cells/ml and allowed to grow until confluence. On the day of study, cell culture media were replaced with 1% FBS experimental media and allowed to remain in quiescence for 12 h. The cellular monolayers were incubated with varying treatment concentrations of free TA solution (1, 10 and 100 μM), TA NPs (10 and 100 μM) and TA NP-TR gel (10 and 100 μM). Culture media were collected at 12 and 72 h. Secreted VEGF in collected culture media was quantified by the ELISA method (Human VEGFA ELISA kit, Thermo Scientific, Waltham, Mass.). The cell protein content was assayed using the BCA protein assay kit after lysing the cells, and VEGF secretion was normalized to total protein. Samples were read using the Synergy H4 plate reader (Biotek Industries, Inc., Winooski, Vt.) with absorbance at 450 nm minus absorbance at 550 nm.

Statistical analyses were performed using Graph Pad Prism (Graph Pad Software, Inc., San Diego, Calif.), Comparisons of the effect of free TA solution, TA NPs and TA NP-TR gels on cell viability and VEGF expression were assessed using paired t tests with a significance level (p) of 0.05, All experiments were carried out in triplicates (n=3) and shown as mean values±SD.

Dynamic Pro plate reader was used to determine the size and PDI of the blank and TA-loaded NPs. The TA NPs were larger in size than the blank NPs. PDI data revealed that all NP formulations had a narrow average size distribution (Table 1).

TABLE 1

NP characterization data carried out in triplicates (n = 3) and represented as the mean value ± SD.

| NP type | Particle size (nm) | PDI |
| --- | --- | --- |
| Blank NP | 125.10 ± 43.89 | 0.014 ± 0.004 |
| TA NP | 208.00 ± 1.00 | 0.005 ± 0.001 |

UV spectroscopy was used to determine the encapsulation efficiency of TA by comparing the absorbance in methanol to standard dilutions of TA in methanol ($r^2$=0.99764) at 240 nm (λmax). It was found that 42.4±0.09% of the TA added during formulation was taken up by the NPs.

Phase transition studies revealed that the 15% w/v aqueous solution of the polymer converts to the gel phase at 40° C. and remains in a gel state until 47° C. The gel phase is broader with higher % w/v solutions. The 20% w/v gel solution demonstrated an optimal transition within physiological conditions and was employed for future studies. FIG. 1 shows the temperature at which each gel formulation transitioned from the solution state to gel state.

Figure 2:
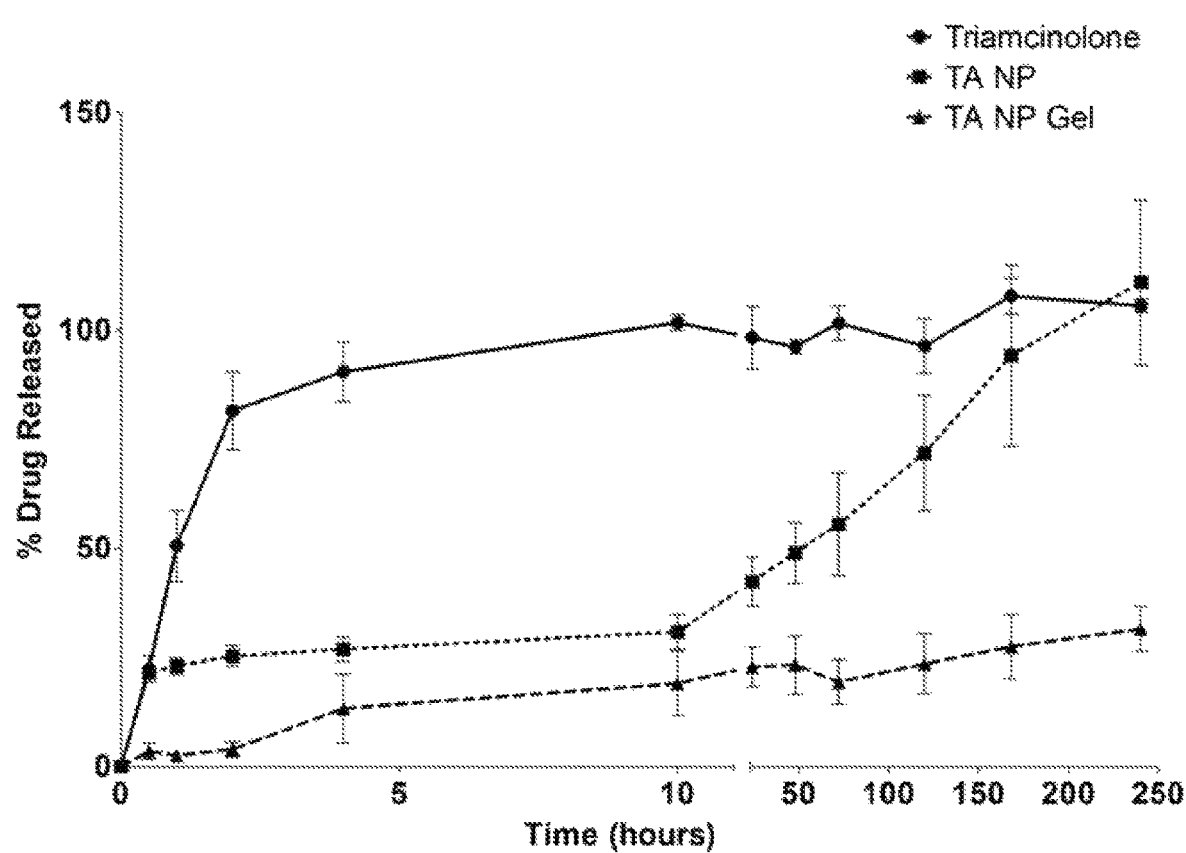
FIG. 2 is a graphical illustration of in vitro release data of the TA NP and TA NP gel as compared to equal concentrations of the TA drug. Samples were analyzed by UV spectroscopy (240 nm, $\lambda_{max}$) at predetermined intervals over a 10-day period (n=3, mean value±SD), in accordance with an embodiment of the present invention.

The release of TA from NPs and TR gel was investigated in 100 ml of PBS and 37° C. FIG. 2 shows the cumulative release profile of the TA NP formulation and TA NP Gel as compared to equal concentrations of the free TA solution. At 48 h; free TA was fully released while the TA NPs released 48.9±7.0% of encapsulated drug and the TA NP Gel released 23.24±6.7% of drug. At 168 h, the cumulative release of TA from the NP formulations was 94.17±20.8%. There is a lack of initial burst release of drug from the NPs. TR Gel had released 31.49±5.1% of drug at 10 days.

Figure 3:
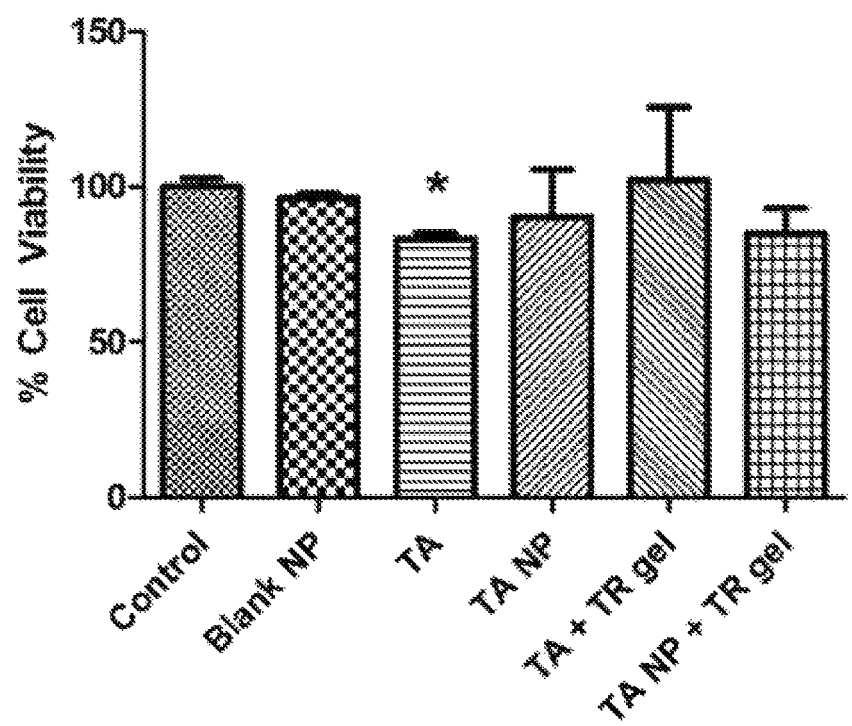
FIG. 3 is a graphical illustration of MTT cytotoxicity data in ARPE-19 cells of equal treatments (10 μM) of the following: Blank NP, TA free drug, TA NPs, TA drug in 20% w/v TR gel, and TA NPs in 20% w/v TR gel as compared to untreated control cells, in accordance with an embodiment of the present invention.
Figure 4:
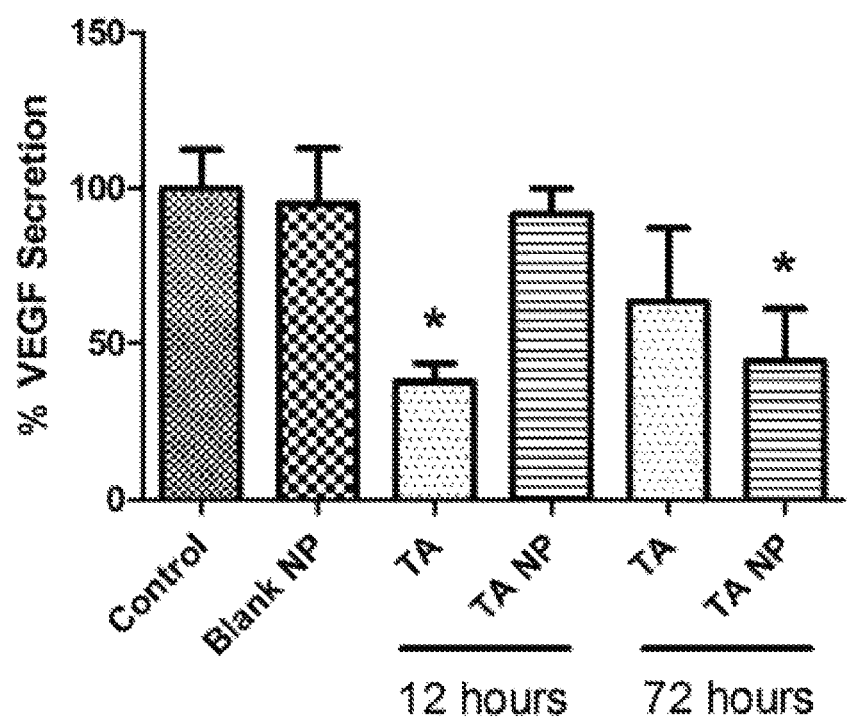
FIG. 4 is a graphical illustration of time-dependent inhibition of VEGF secretion in ARPE-19 cells through equal concentration treatments (100 μM) of blank NPs, TA free drug and TA NPs at 12 and 72 h, in accordance with an embodiment of the present invention.

The cytotoxicity of the DDS was investigated by NM assay in the ARPE-19 cells to determine any possible harm related to its use. FIG. 3 compares the cytotoxicity data of the free TA with equal concentrations (10 μM) of the different TA DDS's described in the present exemplary embodiment: the blank NPs, TA NPs, the TA in 20% w/v TR gel, and the TA NP in 20% w/v TR gel. The free TA induced significant cell death in ARPE-19 cells as compared to the untreated control cells. All other treatments were not significantly cytotoxic in ARPE-19 cells.

Figure 5:
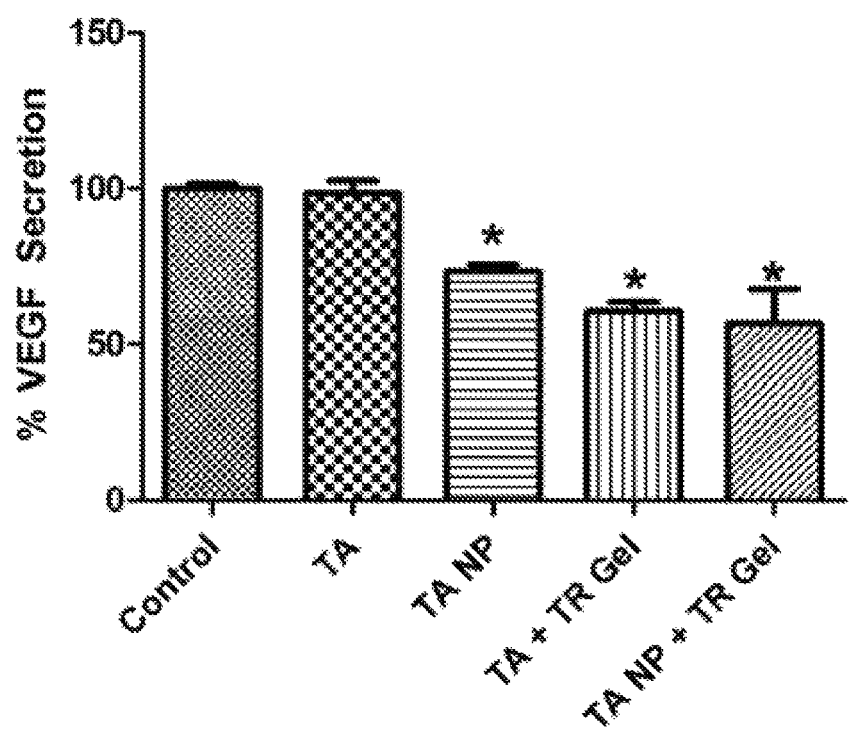
FIG. 5 is a graphical illustration of comparative suppression of VEGF secretion in ARPE-19 cells through equal concentration treatments (10 μM) of TA free drug, TA NPs, TA drug in 20% w/v TR gel, and TA NPs in 20% w/v TR gel at 72 h, in accordance with an embodiment of the present invention.

The effect of the different TA NP formulations on VEGF secretion was studied in ARPE-19 cells. Cells were treated with different concentrations of free TA, TA NPs, TA in 20% w/v TR gel and TA NP in 20% w/v TR gel, for 12 and 72 h. MG. 4 compares the time-dependent suppression of VEGF expression among blank NPs, free TA and TA NPs (100 μM) at 12 and 72 h. The blank NPs did not reduce VEGF expression throughout the time periods tested. The free TA significantly reduced VEGF secretion in 12 h, but TA NPs were not able to do it; however, at 72 h; free TA was unable to significantly reduce VEGF secretion but TA NPs were able to reduce VEGF secretion. FIG. 5 compares the effect of different DDS's (10 μM) on VEGF expression at 72 h: free TA, TA NPs, TA in 20% w/v TR gel and TA NPs in 20% w/v TR gel. The TA NPs, TA in 20% w/v TR gel and TA NPs in 20% w/v TR gel all significantly reduced VEGF expression after 72 h, but the free TA alone had no significant effect.

The emulsion solvent evaporation process was used in the formulation of the polymeric TA NP suspension. Multiple formulations revealed consistent reproducibility with respect to particle size and encapsulation efficiency (data not shown). Particle size data showed that the average size of the NPs increases with drug loaded into the NPs as compared to the blank NPs (180-208 nm). Each of the NP formulations exhibited a unimodal size distribution, suggesting a Gaussian distribution with respect to NP size in each formulation. Particle size, PDI and encapsulation efficiency data were corroborated with previously published studies.

The release of TA from the TA NPs and TR gel was measured in 37° C. PBS over 10 days as compared to the release of the free TA. TA remains stable in solution as demonstrated by release data previously reported. The free TA was completely released from the dialysis membrane in the first 48 h; however, only approximately 48.9±7.0% of the drug was released from each of the NP formulations in as much time. Almost all of the drug was released from the NPs by the end of the 10-day period. The lack of initial burst release suggests that the drug was well encapsulated by the PLGA NP during formulation and none of the drug exists on the surface of the NP. The NP formulation exhibited a sustained release over the 10-day period tested. The release of entrapped drug from a polymer matrix is believed to occur in two stages: the early stage of drug release occurs through diffusion in the polymer matrix, while the latter phases occur through a combination of diffusion and polymer degradation. 49±5.1% of the drug was released from the TR gel at 10 days. Similar results are reported in the literature where TR gel based on PLGA and PEG were able to deliver a 45-kDa protein across the sclera to the retina for up to 14 days. The gelation temperatures of different % w/v formulations of the PLGA-PEG-PLGA TR gel were investigated, it was found that an increasing % w/v of the TR gel solution broadened the temperature range over which the TR gel changes phases from solution to gel to solution (sol-gel-sol). The temperatures over which the 20% w/v TR gel phase transitioned from sol-gel-sol were best in regards to physiological conditions. The 20% w/v TR gel transitions from solution to gel at approximately 32° C., which is the optimum temperature for its easy intraocular injection and phase transition into the gel phase at physiological temperatures. The incorporation of a 10 µM treatment of TA NP formulation into the 20% w/v gel did not produce any cytotoxic effects on ARPE-19 suggesting its safe use in in vivo settings.

NP cytotoxicity studies in ARPE-19 cells showed that the PLGA NP vector is not cytotoxic although treatments with 10 µM free TA are cytotoxic under similar conditions. It was also found that not only is the PLGA vector safe for use in ARPE-19 cells but also that the TA NP formulation and TR gel DDS (with incorporated TA NPs) are not significantly cytotoxic. Concentrations of TA needed to inhibit VEGF secretion have been previously reported. Consistent with those values, the results show that the TA NPs and TR DDS formulations are able to significantly reduce VEGF expression in ARPE-19 cells at 10 and 100 µM over 72 h more effectively than the free TA at equal concentrations. The free TA is able to significantly reduce VEGF expression at the 100-µM concentration in 12 h and similar concentrations take the TA NPs 72 h to reduce VEGF expression, which may be due to the extended release properties of the TA NPs.

As such, in this embodiment of the present invention, a novel DDS is provided for the amelioration of the CNV exhibited in cases of AMD. In this embodiment, the DDS comprises TA encapsulated NPs that are incorporated into 20% w/v TR gels. The TA NPs are spherical and the shape and sizes are compatible in the cells. The NPs exhibited an extended and sustained release of TA as is evident from in vitro release data. Furthermore, the TA NPs and NP-incorporated 20% w/v TR gel did not exhibit cytotoxicity in ARPE-19 cells in concentrations that are shown to significantly reduce ARPE-19 cell viability by free TA alone under the same conditions. The TA NP and NP-incorporated 20% w/v TR gel were able to significantly reduce the expression of VEGF in ARPE-19 cells over 72 h at concentrations less than those required by free TA alone (10 µM TA-loaded DDS versus 100 µM free TA). The biocompatibility and therapeutic potential of the proposed DDS makes it an effective model for the treatment of AMD.

Loteprednol etabonate (LE), a derivative of prednisolone was the first retrometabolically designed steroid. It is a siteactive corticosteroid designed to transform into an inactive metabolite after exerting its therapeutic effect. It contains an ester group at the carbon 20 position, instead of a ketone. Compared to prednisolone acetate, it is less likely to increase ocular pressure and does not lead to cataract formation. Therefore, it is commonly, prepared as a suspension and used topically for anterior segment disorders such as allergy conjunctivitis, anterior uveitis, and postoperative inflammation.

The present invention describes a drug delivery system consisting of loteprednol etabonate encapsulated PLGA-PEG NPs incorporated into TR gel to improve the therapeutic profile of loteprednol etabonate in AMD. The proposed DDS has the potential to significantly improve current therapies against CNV.

In a particular embodiment, Poly(lactic-co-glycolic acid) (PLEA) conjugated with polyethylene glycol (PEG) (PEG-PI-GA) (5050 DLG, mPEG 5000, 5 wt % PEG) was purchased from Lakeshore Biomaterials (Birmingham, Ala.). Loteprednol etabonate was purchased from Selleckchem (Houston, Tex.). Poly(lactide-coglycolide)-b-Poly (ethylene glycol)-b-Poly(lactide-coglycolide) [PLGA-PEG-PLGA (Mn~1,100:1,000:1,100 Da, 3:1 LA:GA) (25% PEG)] thermogelling polymer was purchased from Polyscitech (West Lafayette, Ind.). Phosphate buffered saline (PBS) solution was purchased from Mediatech, Inc (Manassas, Va.). Thiazolyl blue tetrazolium bromide (MTT reagent), acetone and methanol were purchased from Sigma Aldrich (St. Louis, Mo.). All other chemicals used in the embodiment were of analytical grade and were used without any further purification unless specified.

Loteprednol etabonate-loaded NPs (LIE NPs) were prepared using a previously reported nanoprecipitation method. 8 mg of LE and 55 mg of PEGylated PLEA were dissolved in 4 mL acetone (organic phase) and added dropwise to 8 mL of deionized $H_2O$ spinning at 300 rpm overnight to allow full evaporation of the organic phase and the formation of the NP suspension. The NPs were separated by centrifugation at 3,000 rpm for 10 minutes and resuspended in fresh deionized $H_2O$.

Parameters of the NPs were studied by measuring the particle size and polydispersity, index (PDI). The effect of loading LE into the NPs on these parameters was studied by comparing LIE NPs to blank NPs. Particle size and PDI were measured using the Dynamic Pro plate reader (Wyatt Technology Corporation, Santa Barbara, Calif.). The NPs samples were diluted 1:5 in deionized water to fit instrument specifications.

Drug entrapment efficiency was determined by using a previously reported method (20). 1 mL of the NPs solution was centrifuged at 12,000 rpm for 5 minutes. The supernatant was removed and was replaced with 1 mL of methanol and stored at 4° C. overnight. The supernatant of the NPs/methanol solution was diluted 1:5 and measured by UV spectroscopy at a wavelength of 243 nm (λmax). The supernatant was analyzed and compared to a series of standard dilutions of LE in methanol ($r^2$=0.9981). Encapsulation efficiency was determined using the following equation:

$$\% \text{ Entrapment efficiency} = \frac{\text{Actual drug amount}}{\text{Theoretical drug amount}} \times 100$$

SEM was utilized to visualize the surface and physical integrity of LE NPs. JOEL JSM-6490LV (JOEL Industries, Tokyo, Japan) was used to visualize the samples. The samples were diluted according to instrumental specifications and loaded onto aluminum cylinders coated with an adhesive carbon polymer. NP formulations were viewed in 15,000× magnification and 5 kv acceleration voltage was used to visualize the drug loaded NPs.

TR gels were prepared using the cold method. Briefly, the 20% w/v gel was prepared by solubilizing 100 mg of PLGA-PEG-PLGA gel in deionized H2O overnight at 4° C. LE release rate from the NPs was measured by a previously reported method. Dialysis membrane tubing, MWCO 10,000 Da. (Spectrum Laboratories, Rancho Dominguez, Calif.), was soaked in deionized $H_2O$ overnight. NPs solutions were sonicated, and 1 mL was added to the dialysis membrane tubing; tubing was placed into 100 mL of PBS and stirred at 100 rpm at 37° C. 1 mL samples were removed at predetermined intervals over 7 days and replaced with fresh PBS. Samples were analyzed using UV spectroscopy at a wavelength of 243 nm (λmax) and compared to standard dilutions of LE in PBS ($r^2$=0.9915) to determine the percentage of drug released over 10 days.

LE release from the TR gel was measured by allowing 200 µL of LE NPs in 20% w/v polymer solution to gel by placing in incubator at 37° C. for 5 minutes. After gelling, release was initiated by adding 2.5 mL PBS. 1 mL samples were removed at predetermined intervals over 7 days and replaced with fresh PBS.

Human retinal pigment epithelium, ARPE-19, cells (ATCC # CRL-2302) were grown in 1:1 Dulbecco's Modified Eagle's Medium and Ham's F12 Medium (Mediatech, Inc., Manassas, Va.) with 10% fetal bovine serum and 100 U/mL penicillin/streptomycin (Sigma Aldrich, St. Louis, Mo.). The cultures were maintained in a humid environment at 5% $CO_2$ and 37° C.

Cytotoxicity was assessed in ARPE-19 cells by the 3-(4, 5-dimethylthiazol-2-yl)-2,5-diphenyltetrazolium bromide salt (MTT) assay. Briefly, cells were seeded in 24-well plates at a density of 5×104 cells/mL for 24 hours to achieve confluence before treatment. Cells were exposed to free LE solution, LE NPs, and LE NPs-TR gel at varying concentrations (0, 1, 10, 100 µM) for 24 hours after which the MTT assay was performed. Cell culture media were aspirated and 300 µL of MTT reagent solution (1 mg/mL) was added to each well. Cells were incubated at 37° C. and 5% $CO_2$ for 4 hours, after which the MTT reagent solution was aspirated and 500 µL of DMSO was added to each well. Plates were allowed to shake gently for 10 minutes before being read by Synergy H4 plate reader (Biotek Industries, Inc., Winooski, Vt.) at absorbance of 570 nm.

ARPE-19 Cells Coumarin-6-loaded NPs were prepared by the method outlined above. In lieu of LE, 15 µL of coumarin-6 (1 mg/ml acetone stock solution) was added. ARPE-19 cells were seeded at 10,000 cells per well in a four-well chamber slide. The cells were incubated for 24 hours to achieve 70% confluence. The medium was aspirated and cell monolayer was washed three times with PBS. 500 µL media containing 50 µg of coumarin-loaded NPs was added to the wells and incubated for 2 hours. After 2 hours, cells were washed with PBS three times, and treated with DAPI for nuclear staining and Cell Mask Deep Red for membrane staining. The slide was then examined by confocal microscopy with a magnification of 60×.

ARPE-19 cells were seeded onto 24-well plates at 5×104 cells/mL and allowed to grow until confluence. On the day of study, cell culture media were replaced with 1% FBS experimental media and allowed to remain in quiescence for 12 hours. The cellular monolayers were incubated with varying treatment concentrations of free LE solution (1, 10 µM), LE NPs (10 µM), and LE NPs-TR gel (10 µM). Culture media were collected at 12 and 72 hours. Secreted VEGF in collected culture media was quantified by the ELISA method (Human VEGFA ELISA kit, Thermo Scientific, Waltham, Mass.). The cell protein content was assayed using the BCA protein assay kit after lysing the cells and VEGF secretion was normalized to total protein. Samples were read by using the Synergy H4 plate reader (Biotek Industries, Inc., Winooski, Vt.) with absorbance at 450 nm minus absorbance at 550 nm.

Statistical analyses were performed using GraphPad Prism (GraphPad Software, Inc., San Diego, Calif.). Comparisons of the effect of free LE solution, LE NPs, and LE NPs-TR gels on cell viability and VEGF expression were assessed using paired t-tests with a significance level (p value) of 0.05. All experiments were carried out in triplicates (n=3) and shown as mean values±SD.

Dynamic Pro plate reader was used to determine the size and PDI of the blank and LE-loaded NPs. The LE NPs were larger in size than the blank NPs. PDI data revealed that all NPs formulations had a normal size distribution (Table 1) with PDI value less than 1.

| NP Type | Particle size (nm) | PDI |
| --- | --- | --- |
| Blank NPs | 125.10 ± 43.89 | 0.014 ± 0.004 |
| LE NPs | 168.00 ± 23.18 | 0.0142 ± 0.0023 |

UV spectroscopy was used to determine the entrapment efficiency of LE by comparing the absorbance in methanol to standard dilutions of LE in methanol ($r^2$=0.9981) at 243 nm (λmax). The LE NPs formulation showed an entrapment efficiency of 82.6±0.01% which was satisfactory.

SEM was used to visualize the morphology of LE NPs. Surface analysis of NPs formulations showed that physical integrity was maintained by all samples. A SEM visualization of loteprednol etabonate-loaded nanoparticles shows round morphology. Samples were diluted 1:10 and visualized by SEM. Samples were read at 15,000× magnification and 5 kV acceleration voltage, in accordance with an embodiment of the present invention. Size and size distribution of the NPs formulation visualized through SEM corroborated with data obtained by DLS.

Figure 6:
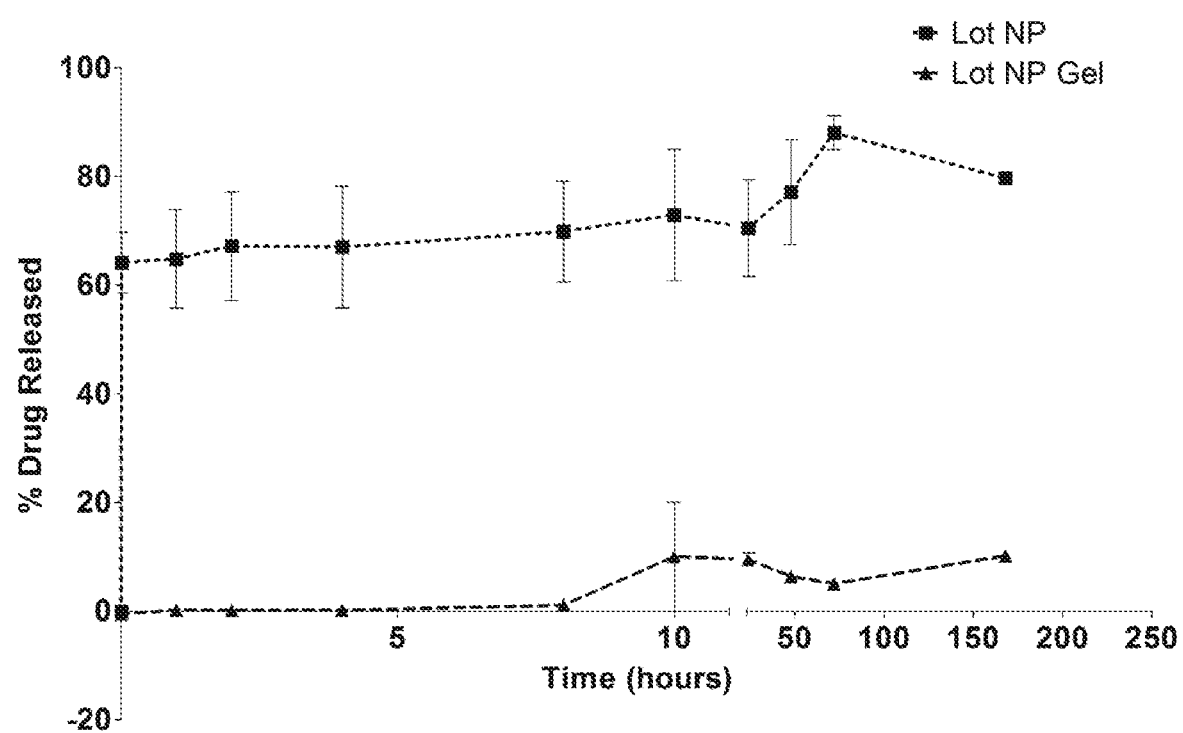
FIG. 6 is a graphical illustration of in vitro release data of the loteprednol etabonate nanoparticles (LE NP) compared to LE NP gel, in accordance with an embodiment of the present invention.

The release of LE from NPs and TR gel was conducted in vitro in a beaker with 100 mL of PBS at 37° C. FIG. 6 shows the cumulative release profile of the Lot NPs formulation compared to the LE NPs TR gel. At 72 hours, the LE NPs formulation had released 88% of the encapsulated drug while the LE NPs TR gel formulation had released 5% of drug. At 168 hours, the TR gel had released 10% of drug.

Figure 7:
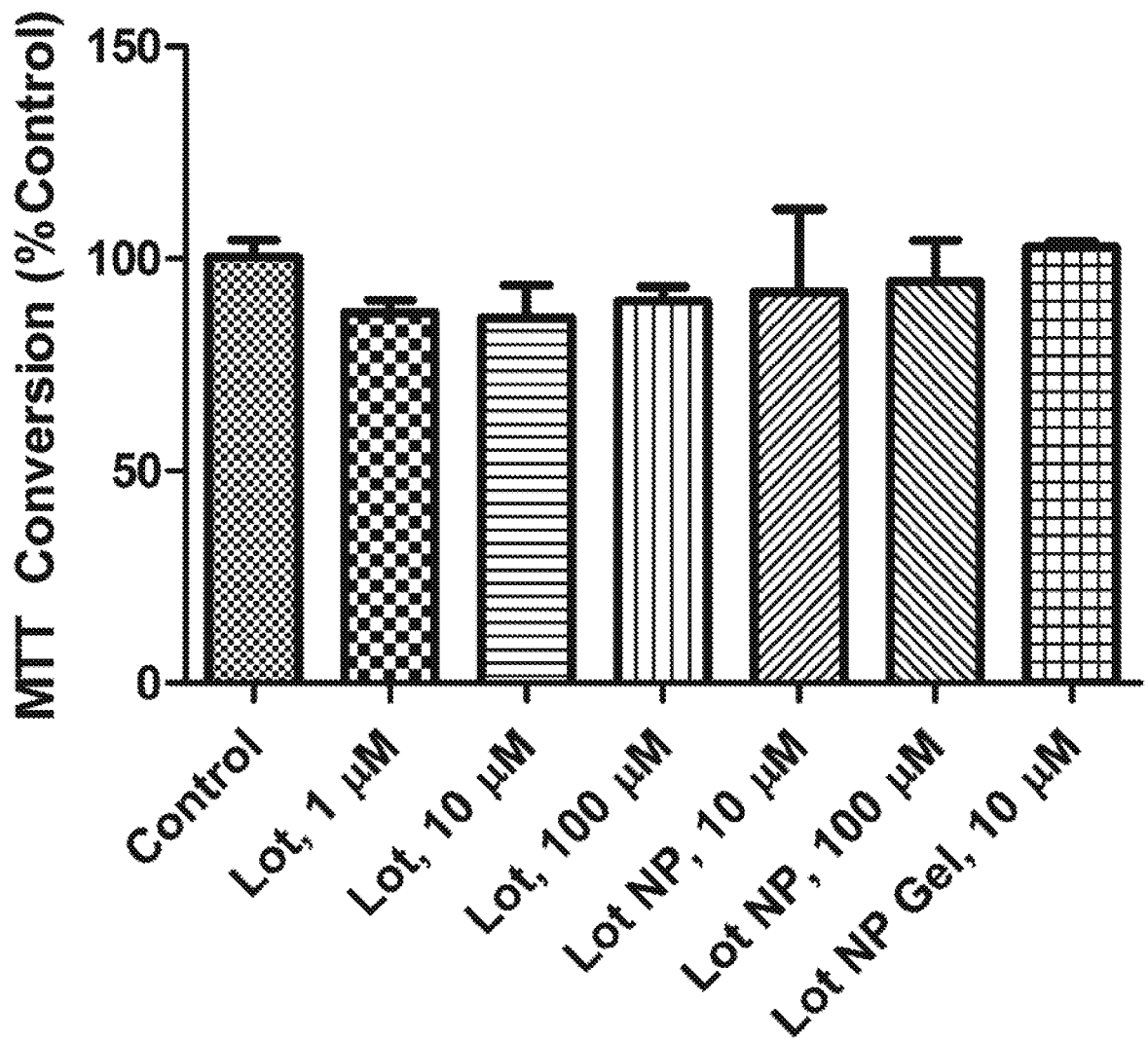
FIG. 7 is a graphical illustration of MTT cytotoxicity data in ARPE-19 cells of increasing concentrations of loteprednol etabonate (LE) free drug, LE NPs, and LE NPs in 20% w/v TR gel as compared to untreated control cells, in accordance with an embodiment of the present invention.

The cytotoxicity of the DDS was investigated by MTT assay in the ARPE-19 cells to determine any possible harm related to its use. FIG. 6 compares the cytotoxic effects of free LE with equal concentrations of the LE NPs and LE NPs in 20% w/v TR gel. FIG. 7 is a graphical illustration of MTT cytotoxicity data in ARPE-19 cells of increasing concentrations of loteprednol etabonate (LE) free drug, LE NPs, and LE NPs in 20% w/v TR gel as compared to untreated control cells. Experiments were carried out in triplicates (n=3) and quantified by absorbance reading at 570 nm. Data is represented as mean±SD. Free LE had no impact on cell viability in ARPE-19 cells as compared to the untreated control cells. All other treatments were not significantly cytotoxic in ARPE-19 cells.

Figure 8:
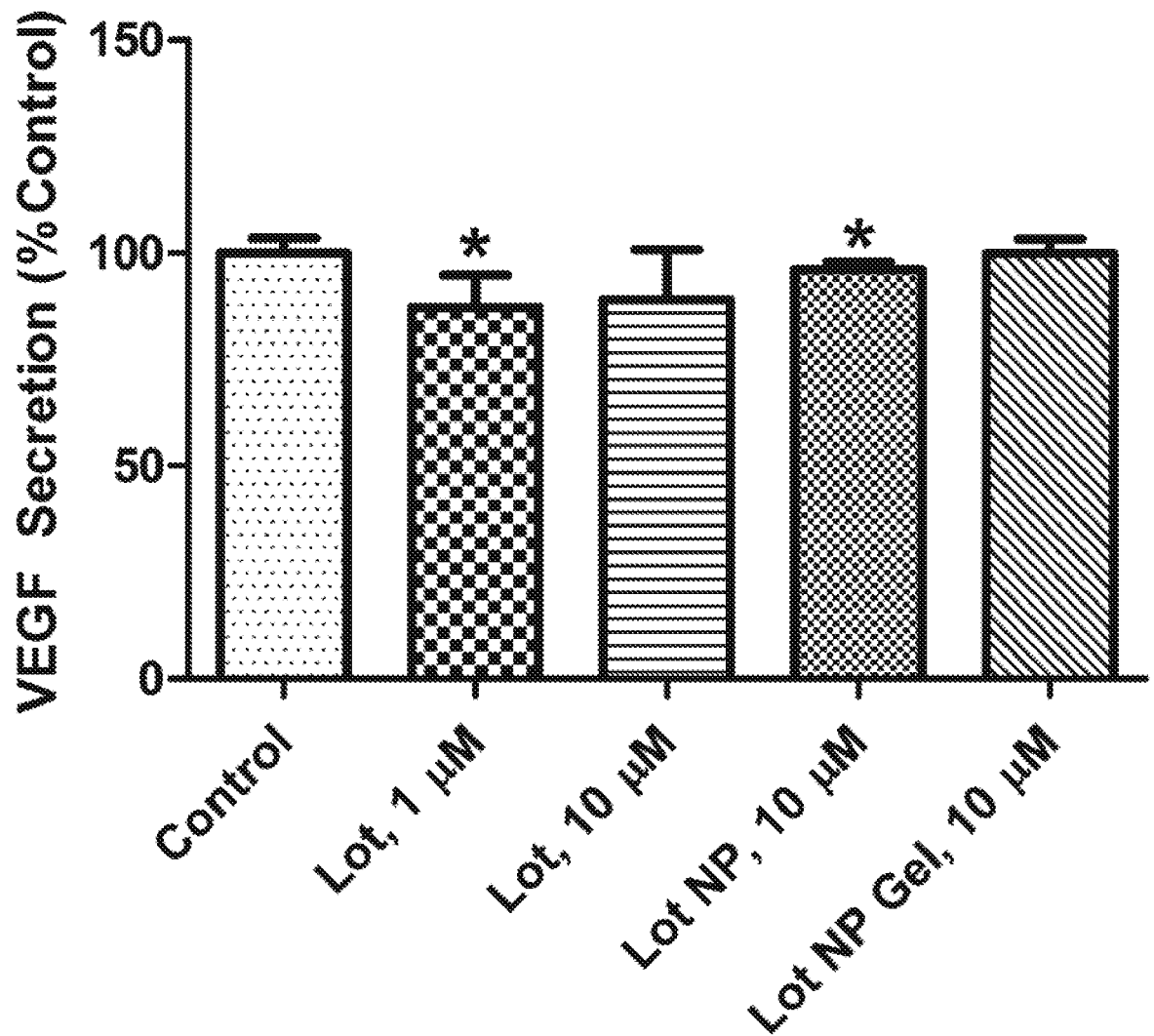
FIG. 8 is a graphical illustration of comparative suppression of VEGF secretion in ARPE-19 cells through increasing concentrations (1, 10, μM) of loteprednol etabonate (LE) free drug, LE NPs, and LE NP gel at 12 hours, in accordance with an embodiment of the present invention.
Figure 9:
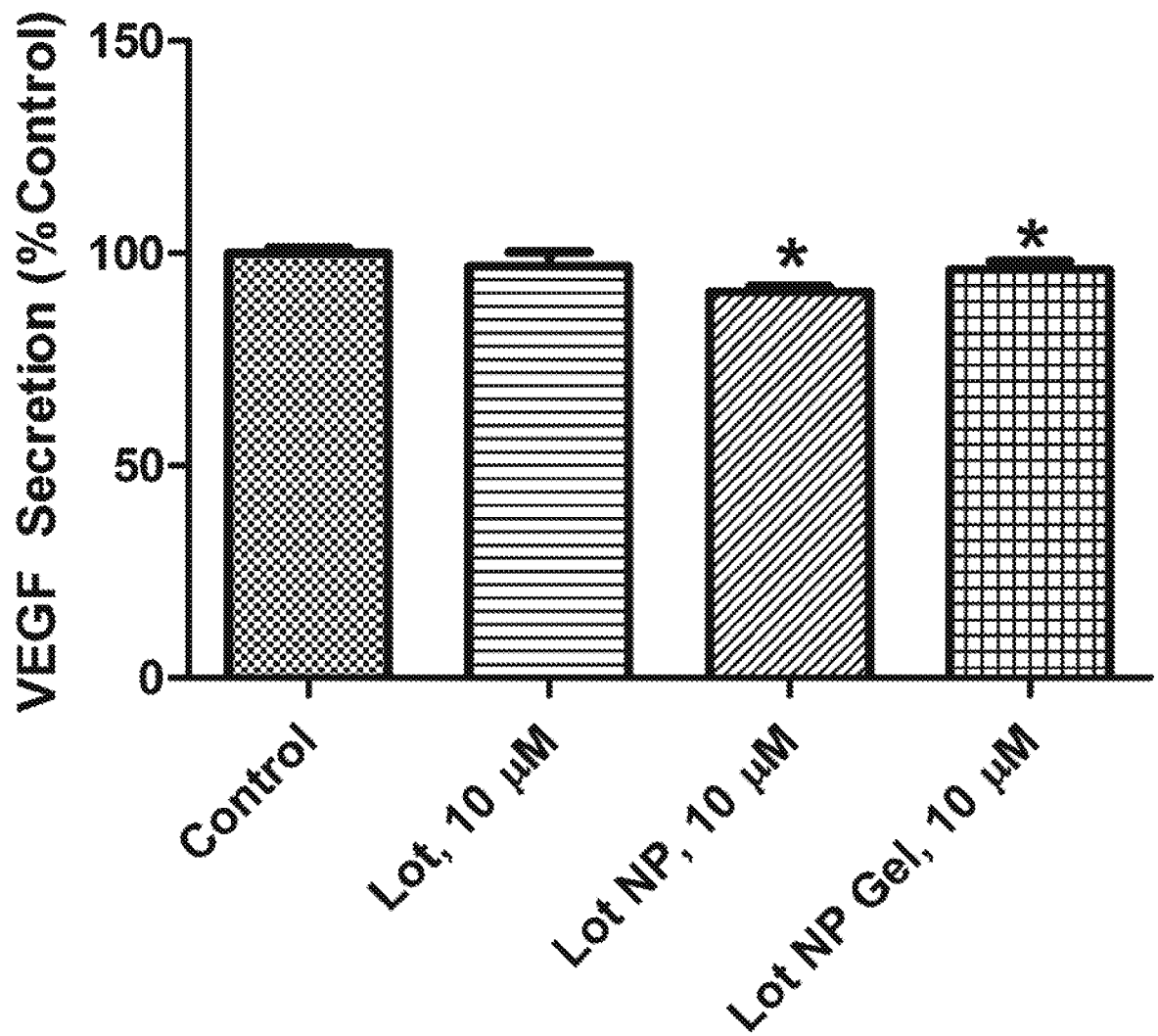
FIG. 9 is a graphical illustration of comparative suppression of VEGF secretion in ARPE-19 cells through equal concentration treatments (10 μM) of LE free drug, LE NPs, and LE NPs in 20% w/v TR gel at 72 hours, in accordance with an embodiment of the present invention.

The effect of the LE DDS on VEGF secretion was studied in ARPE-19 cells. Cells were treated with different concentrations of free LE solution, LE NPs, and LE NPs in 20% w/v TR gel, for 12 and 72 hours. FIG. 8 compares the suppression of VEGF expression between free LE solution, LE NPs and the LE NPs TR gel at 12 hours. Free LE solution at 1 µM and 10 µM showed reduction in VEGF expression compared to media control. LE NP at 10 µM was used for the VEGF expression study due to slower release characteristic of the NPs. Moreover, the preliminary data have shown better VEGF expression reduction at this concentration. LE NPs at 10 µM slightly reduced VEGF secretion while NPs TR Gel at 10 µM did not reduce VEGF secretion significantly in 12 hours compared to the control (p value <0.05) as concluded by paired t-test. However, the paired t-test results indicated that both NPs and NPs TR Gel at 10 µM significantly reduced VEGF secretion in 72 hours (p value <0.0), as shown in FIG. 9. This may be due to controlled release of the drug from NPs polymer matrix and NPs TR Gel. The VEGF expression for NPs and NPs TR Gel at 10 µM was reduced to 90.99±1.29% and 96.24±1.91% respectively. The % reduction VEGF expression of NPs TR Gel was observed as lower than NPs due to further delayed release of the drug from the gel matrix compared to NPs alone.

Polymeric LE NPs were prepared by the emulsion solvent evaporation method with reproducible and satisfactory particle size and entrapment efficiency. The particle size of unloaded NPs was 125 nm while drug loaded NPs was 168 nm. Both NPs formulations showed a normal size distribution with PDI value less than 1. Particle size, PDI, and entrapment efficiency data were corroborated with previously published studies. The rate of drug release from the NPs and TR gel was measured using dialysis method in PBS at 37° C. over the course of 7 days. At 72 hours, the LE NPs exhibited 88% drug release while the LE NP Gel had released 5% of drug. The TR gel had released 10% of drug at 168 hours. Both formulations exhibited sustained release pattern; however, the drug release from the TR gel was further slower due to drug release via polymer degradation. Polymer matrices release encapsulated drug in two phases: the first phase of drug release occurs via diffusion and the second phase is by diffusion and polymer degradation. MTT cytotoxicity studies in ARPE-19 cells showed no cytotoxicity after 24-hour exposure to free LE solution, LE NPs, or LE TR gel. LE was not expected to have any toxic effects as it was formulated to prevent any physiological side effects. The LE NP and LE NP incorporated TR gel DDS were observed to be safe to use in ARPE-19 cells. Additionally, the NPs were localized into the ARPE-19 cells within 2 hours. To support these data, recent in vivo studies have shown that NPs were localized within 6 hours at the retinal pigment epithelium of healthy rat after intravitreal injections. LE NPs and LE NP TR gel were able to significantly reduce VEGF expression in ARPE-19 cells at 10 µM over 72 hours more effectively than equal concentrations of LE drug solution (p<0.05). Free LE drug solution significantly reduced VEGF expression within 12 hours compared to control (p<0.05) while drug loaded NPs and NPs TR Gel exhibit their effect after 72 hours due to the extended release properties of the NPs and the gel.

This embodiment of the present invention provides for the use of a novel DDS for controlled release of LE for potential treatment of wet AMD by reducing the frequency of intravitreal injections. The proposed DDS of this embodiment showed sustained in vitro release and showed no cytotoxicity in in vitro experiments using ARPE-19 cells. The DDS of LE was able to significantly reduce the expression of VEGF in ARPE-19 cells over 72 hours compared to LE solution alone. The biocompatibility, low toxicity and therapeutic potential of the proposed DDS make it an ideal model treating AMD and reducing intravitreal injection frequency.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A drug delivery system for the treatment of age-related macular degeneration (AMD), the drug delivery system comprising:
    a sustained-release formulation comprising;
    a PLGA-PEG-PLGA thermoreversible (TR) hydrogel; and
    PLGA nanoparticles encapsulating loteprednol etabonate (LE) incorporated into the PLGA-PEG-PLGA thermoreversible (TR) hydrogel, wherein the PLGA nanoparticles have an entrapment efficiency of LE equal to 82.6±0.01% and wherein the PLGA nanoparticles have an average particle size equal to 168.00±23.18 nm;
    wherein the sustained-release formulation provides a burst-free, sustained release of the TA during both a diffusion phase and a polymer degradation phase of the sustained release.

2. The drug delivery system of claim 1, wherein the PLGA-PEG-PLGA TR hydrogel is a 20% w/v TR hydrogel.

3. The drug delivery system of claim 1, wherein the PLGA nanoparticles are substantially spherical.

4. A method for the treatment for age-related macular degeneration (AMD), the method comprising:
    administering one or more intravitreal injections of a sustained-release formulation comprising PLGA nanoparticles encapsulating loteprednol etabonate (LE) incorporated into a PLGA-PEG-PLGA thermoreversible (TR) hydrogel to a patient, wherein the sustained-release formulation provides a burst-free, sustained release of the LE during both a diffusion phase and a polymer degradation phase of the sustained release and wherein the PLGA nanoparticles have an entrapment efficiency of LE equal to 82.6±0.01% and wherein the PLGA nanoparticles have an average particle size equal to 168.00±23.18 nm.

5. The method of claim 4, wherein the PLGA-PEG-PLGA TR hydrogel is a 20% w/v TR hydrogel.

6. A method of manufacturing a drug delivery system for the treatment of age-related macular degeneration (AMD), the method comprising;
    forming PLGA nanoparticles encapsulating a loteprednol etabonate (LE); and
    incorporating the PLGA nanoparticles encapsulating LE into a PLGA-PEG-PLGA thermoreversible (TR) hydrogel to from a sustained-release formulation, wherein the sustained-release formulation provides a burst-free, sustained release of the LE during both a diffusion phase and a polymer degradation phase of the sustained release and wherein the PLGA nanoparticles have an entrapment efficiency equal to 82.6±0.01% and wherein the PLGA nanoparticles have an average particle size equal to 168.00±23.18 nm.

7. The method of claim 6, wherein the PLGA-PEG-PLGA TR hydrogel is a 20% w/v TR hydrogel.

8. The method of claim 6, wherein the loteprednol etabonate encapsulated nanoparticles are substantially spherical.

* * * * *